US011369700B2

(12) United States Patent
Frank et al.

(10) Patent No.: US 11,369,700 B2
(45) Date of Patent: Jun. 28, 2022

(54) DOTMP KIT FORMULATIONS FOR RADIOISOTOPES

(71) Applicant: IsoTherapeutics Group, LLC, Angleton, TX (US)

(72) Inventors: R. Keith Frank, Lake Jackson, TX (US); Jaime Simon, Angleton, TX (US); Kelli R. Jay, Brazoria, TX (US)

(73) Assignee: IGL Pharma Inc., Angleton, TX (US)

( * ) Notice: Subject to any disclaimer, the term of this patent is extended or adjusted under 35 U.S.C. 154(b) by 62 days.

(21) Appl. No.: 16/866,001

(22) Filed: May 4, 2020

(65) Prior Publication Data

US 2020/0261607 A1 Aug. 20, 2020

Related U.S. Application Data

(63) Continuation-in-part of application No. 15/821,974, filed as application No. PCT/US2016/033900 on May 24, 2016, now abandoned.

(60) Provisional application No. 62/166,051, filed on May 25, 2015.

(51) Int. Cl.
| | | |
|---|---|---|
| A61K 51/04 | (2006.01) | |
| A61K 47/02 | (2006.01) | |
| A61P 35/00 | (2006.01) | |
| A61K 9/19 | (2006.01) | |

(52) U.S. Cl.
CPC ............. *A61K 51/0482* (2013.01); *A61K 9/19* (2013.01); *A61K 47/02* (2013.01); *A61P 35/00* (2018.01)

(58) Field of Classification Search
CPC .......... A61K 51/04; A61K 47/02; A61K 9/19; A61P 35/00
See application file for complete search history.

(56) References Cited

U.S. PATENT DOCUMENTS

| | | | |
|---|---|---|---|
| 4,898,724 A | 2/1990 | Simon et al. | |
| 5,059,412 A | 10/1991 | Simon et al. | |
| 5,064,633 A | 11/1991 | Simon et al. | |
| 5,066,478 A | 11/1991 | Simon et al. | |
| 7,696,331 B2 * | 4/2010 | Fritzberg | ................ A61P 43/00 424/9.1 |
| 2002/0176818 A1 | 11/2002 | Fritzbeg | |
| 2010/0068151 A1 | 3/2010 | Rosenblum | |

FOREIGN PATENT DOCUMENTS

| | | | | |
|---|---|---|---|---|
| CA | 2926652 | * | 4/2015 | ......... A61K 51/0482 |
| CA | 2926652 A1 | | 4/2015 | |
| EP | 0375376 A2 | | 6/1990 | |
| WO | 1990/006776 A1 | | 6/1990 | |
| WO | 1995/029706 A1 | | 11/1995 | |
| WO | 2003/051403 A1 | | 6/2003 | |
| WO | 2011/149844 A1 | | 12/2011 | |
| WO | 2014/140095 A1 | | 9/2014 | |
| WO | 2014/204800 A1 | | 12/2014 | |

OTHER PUBLICATIONS

Das, T. et al., Applied Radiation and Isotopes, vol. 57, 2002, pp. 177-184.

\* cited by examiner

*Primary Examiner* — Michael G. Hartley
*Assistant Examiner* — Jagadishwar R Samala
(74) *Attorney, Agent, or Firm* — Technology Law PLLC; Karen L. Kimble

(57) ABSTRACT

This invention relates to a Kit formulation to prepare a radioactive, bone-seeking, pharmaceutical drug that has high radiochemical purity (RCP) in a fast, facile and reproducible process. The Kit has at least two vials and a two-part buffer system with instructions on how to make the drug formulation in a radiopharmacy. The drug formulations of this invention can be conveniently and reproducibly prepared with better delivery of the drug to mammals, better radiochemical purity of the formulation for use in treating a mammal having bone pain, one or more calcific tumors or needing bone marrow suppression or bone marrow ablation.

4 Claims, 2 Drawing Sheets

DOTMP KIT FORMULATIONS FOR RADIOISOTOPES

GOVERNMENT LICENSE RIGHTS

This invention was made with government support under SBIR grant number R44CA150601 awarded by NIH. The government has certain rights in the invention.

BACKGROUND OF THE INVENTION

Field of the Invention

This invention relates to a Kit (defined below in the Glossary) formulation for bone-seeking radioactive metal-chelant compositions having DOTMP as the chelant that are suitable for administration to a patient or animal having bone pain, one or more calcific tumors, or needing bone marrow suppression or bone marrow ablation.

Description of Related Art

Numerous pharmaceutical formulations for injection into a patient have been developed. Many formulations for injection into a mammal use buffers for various purposes. For example, some cancer treatment formulations for bone tumors containing N-3-bis(2-chloroethyl)-1,3,2-oxazaphosphinan-2-amide-2-oxide (ifosfamide, U.S. Pat. No. 6,906,047) use one buffer and no radioisotope.

U.S. Pat. No. 8,716,279 describes a formulation of benzodiazepine compositions that are formulated for intranasal administration, comprising a binary solvent system comprising a first solvent in which the benzodiazepine is soluble, the first solvent capable of penetrating nasal mucosal tissue, and a second solvent in which the benzodiazepine in less soluble. Thus a two component system is used but no radioisotope is present.

A radiopharmaceutical "kit" is a vial or vials containing necessary components that are combined, following prescribed instructions, with a radioisotope to prepare a radiopharmaceutical. This preparation is generally performed at a radiopharmacy, which then transports the drug to a nearby clinical facility for administration. The advantages of such systems are that kits can have long shelf lives and can be stored on-site at a radiopharmacy. Medical radioisotopes generally have short half-lives (e.g. Tc-99m is 6 hr and Y-90 is 64 hr) and once combined into a radiopharmaceutical can begin to radiolytically degrade the other components of the drug.

Examples of kits used to prepare radiopharmaceuticals in this fashion are Cardiolite® (trademark of Lantheus Medical Imaging, Inc.) kit for the preparation of technetium Tc99m sestamibi (NDC 11994-001), Ceretec™ (trademark of GE Healthcare Limited) kit for the preparation of technetium Tc99m exametazime (NDC 17156-022) and Zevalin® (trademark of RIT Oncology, LLC) kit for the preparation of yttrium Y-90 ibritumomab tiuxetan (NDC 68152-103).

Radiopharmaceuticals based on metal-chelant complexes have been used to diagnose and treat bone cancer. Another example is Quadramet® (trademark of Lantheus Medical Imaging, Inc.), a commercially available chelate formed between Sm-153 and ethylenediaminetetramethylenephosphonic acid (EDTMP) that is currently indicated for the pain associated with bone metastases (U.S. Pat. No. 4,898,724). Typical dosages are 1 mCi of Sm-153 per kg body weight of the patient. Thus for a 70 kg patient the dosage would be 70 mCi. Quadramet is produced at a central facility, dispensed and shipped frozen on dry ice in order to reduce radiolytic degradation. This formulation is not a kit but rather the final formulation ordered for a specific patent and shipped to the radiopharmacy to determine the dose for the patient.

U.S. Pat. No. 5,066,478 teaches a kit for the preparation of Sm-153 EDTMP that was developed but was never commercialized. This kit was made by lyophilizing EDTMP and an empirically determined excess of NaOH. The lyophilized chelant was reconstituted with Sm-153 in 5 mL of 0.1 N HCl or $HNO_3$, mixed well and the desired Sm-EDTMP complex was formed having the correct pH for injection. The ratio of EDTMP to Sm was about 300:1. However, a concern was the presence of excess chelant which can bind to calcium ions and potentially stop the heart. Therefore a further kit having 1 eq. of calcium was also made (EP Patent 462,787). The lyophilized vial contained Ca-EDTMP and excess NaOH.

U.S. Pat. No. 5,059,412 teaches the use of Sm-153, Gd-159, Ho-166, Lu-177 and Yb-175 chelates with chelants derived from the 1,4,7,10-tetraazacyclododecane moiety including 1,4,7,10-tetraazacyclododecanetetramethylenephosphonic acid (DOTMP), while U.S. Pat. No. 5,064,633 teaches the above metals plus Y-90. Compositions of Sm, Gd, Ho, Lu and Y with DOTMP comprising predominately non-radioactive metal with the corresponding radioactive metal (e.g. Sm-152 with Sm-153 at µCi levels) were prepared and biodistribution data in rats was obtained. A kit formulation was made that had a first vial containing DOTMP and an empirically determined amount of NaOH which was reconstituted with Ho-166 in 5.0 mL of 0.1 N HCl or $HNO_3$ to form a Ho-DOTMP complex at pH 9-10. It is crucial that the pH not exceed 11 or metal hydroxide will be formed. Likewise if the pH falls below 8, the DOTMP is protonated and the formation of the complex is impeded. The volume of acid added was critical to achieving this proper pH range so an automated syringe pump system was used to assure precise delivery of this volume. No buffers were used to achieve this pH range.

US Published Appln. 20020176818 teaches that Ho-166-DOTMP, a bone marrow suppressing radionuclide composition, is formed by adding a Ho-166 salt, such as the chloride or nitrate in aqueous HCl (0.1-1N) or $HNO_3$, to a sterile, evacuated vial containing at least 3 equivalents of DOTMP in aqueous base (KOH, NaOH and the like). Similar pH control issues are present as before in U.S. Pat. No. 5,059,412. After stirring at a pH of 10.5, for 10 minutes, the pH is then adjusted to 7-8 by adding phosphate buffer and a stabilizing agent such as ascorbic acid. Complexation of >99% is achieved.

A therapeutically effective biodistribution (fate of the activity after administration to a mammal) for a therapeutic bone agent includes high bone uptake, low soft tissue uptake, rapid clearance of the activity not associated with bone, and high lesion-to-normal bone ratio. Compositions that do not have all of these characteristics are detrimental to the patient. For example, high soft tissue uptake would result in the patient receiving a high radiation dose to the liver, spleen or other soft tissue leading to undesirable side effects.

One difficulty in many radionuclide complex formulations is obtaining a high radiochemical purity (RCP) of the complex, as well as maintaining the RCP after it is made until it is injected. The radionuclide causes radiolytic degradation of the complex over time. Having a formulation that has a high RCP for injection, while still being reliable and reproducible to make, has proven difficult.

Clearly, there is a need for a product with a high RCP while controlling the process to prepare it.

BRIEF SUMMARY OF THE INVENTION

The present invention provides a non-radioactive Kit formulation that is used to prepare a radioactive drug, which drug is used for the treatment of a mammal comprising administration to the mammal having bone pain, one or more calcific tumors, or in need of a bone marrow suppressing or ablation procedure. The invention provides a pharmaceutically-acceptable formulation of a Radioisotope chelate composition made from the Kit, said drug comprising a therapeutically effective amount of the complex. The Kit possesses a two-part buffer system, namely, Carbonate followed by Phosphate. The chelate is prepared from a Radioisotope selected from a group consisting of Sm-153, Gd-159, Ho-166, Lu-177 and Y-90 and DOTMP or a physiologically-acceptable salt thereof, which is part of one of the components of the Kit. The drug is prepared from the components of the Kit. The process to prepare the drug from this Kit is provided as instructions with the Kit, as a package insert, or available on-line with the purchase of the Kit.

The present invention provides a pharmaceutically-acceptable Kit formulation for the preparation of a radioactive bone-seeking drug comprising at least two components, having a two-part buffering system, including instructions for its use, for preparing a pharmaceutically-acceptable drug formulation of a Radioisotope-DOTMP chelate, wherein the Kit components are:

Vial 1: lyophilized DOTMP, Carbonate and NaOH or KOH;

Vial 2: optionally a Calcium solution in a pharmaceutically-acceptable aqueous solvent; and Vial 3: a Phosphate buffer in a pharmaceutically-acceptable aqueous solvent at a pH of about 7, optionally with pharmaceutically-acceptable preservatives, diluents, and excipient;

provided that when then Kit is constituted to form the drug at the time of use, a Radioisotope selected from the group consisting of Sm-153, Gd-159, Ho-166, Lu-177, and Y-90 in HCl or $HNO_3$ is added to Vial 1 to achieve a pH of 9-10 and then adding Vial 2 and Vial 3 to form the drug.

The formulation of this invention comprises a chelant composition as a Kit having at least two separate components that form the Kit, which includes a two-part buffer system, which components are mixed in a prescribed manner with a Radioisotope to form the chelate composition at the appropriate time prior to its use as a drug.

The present invention provides a process for the preparation of a pharmaceutically-acceptable drug formulation using the Kit described above, which comprises the steps of:

a) reconstituting the lyophilized Vial 1 having Carbonate, DOTMP and NaOH or KOH, with a Radioisotope in HCl or $HNO_3$; and
wherein the Carbonate buffers at pH to about 9-10 so that the Radioisotope-DOTMP complex forms readily with an initial RCP of at least 97%;

b) optionally adding to Vial 1, Vial 2, a Calcium solution, to the Radioisotope-DOTMP of step a); and c) adding Vial 3, Phosphate buffer, to the prior formed solution of step a) or b) to bring the pH to about 7-8 suitable for injection into a mammal The two-part buffer system provides critical pH control during two separate steps in the preparation process of the drug. Specifically, the solution from which the lyophilized component 1 is prepared has a large excess of NaOH or KOH over the Carbonate present thereby having a very high pH but no buffering capacity. The large excess of NaOH or KOH is present to neutralize the future addition of Radioisotope solution in HCl or $HNO_3$ when the Kit is used to prepare the drug. Once the acid is neutralized, the small amount of Carbonate now provides buffering of the solution at pH of 9-10. This pH of 9-10 is the optimal range for chelate formation. When the prescribed volume of acid is added to component 1 no further pH adjustment is required. Thus this first step of the Kit process is fast and facile. When component 3 (Phosphate) is added, the amount of Phosphate present is designed to overwhelm the amount of Carbonate present thereby buffering the final drug solution at pH 7-8 and providing optimal osmolality suitable for injection. Therefore, the Kit provides for the preparation of the drug in a fast and facile manner without further pH adjustments or other manipulations while still providing RCP of at least 97% in a consistent and reproducible manner by the radiopharmacy. Radiolytic degradation of the drug is minimized after its preparation by the radiopharmacy as the drug may be injected a short time thereafter to a mammal. No stabilizing agent (e.g. ascorbic acid) is required but may optionally be used.

The drug made from the above Kit is used in a method of treating a mammal having disease causing bone pain, one or more calcific tumors or needing bone marrow suppression or bone marrow ablation by administration to said mammal this drug formulation.

DETAILED DESCRIPTION OF THE INVENTION

Figure 1:
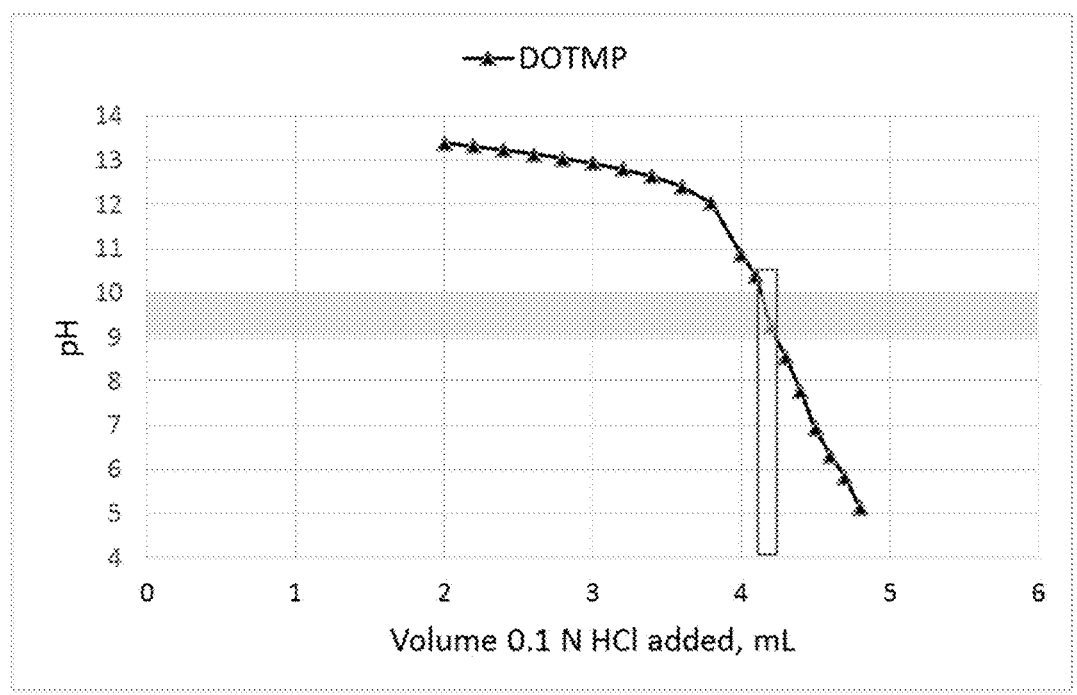
FIG. 1 graphically shows the data for NaOH and DOTMP titrated with 0.1 N HCl. The steep titration curve illustrates the very narrow volume range of acid required to achieve the desired pH range of 9-10 for optimal chelation.

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and PCT published applications have been incorporated by reference. However, the text of such patents is only incorporated by reference to the extent that no conflict exists between such text and other statements set forth herein. In the event of such conflict, then any such conflicting text in such incorporated by reference US patent or PCT application is specifically not so incorporated in this patent.

Glossary
- Calcium solution means an aqueous solution of calcium such as can be prepared from calcium chloride or calcium nitrate
- Carbonate means pharmaceutically-acceptable $NaHCO_3$, $Na_2CO_3$, $KHCO_3$ or $KCO_3$ and mixtures thereof which, under appropriate conditions, have the ability to buffer at pH 9-10
- Ci means curies
- Chelate and Complex are used interchangeably and mean a metal bound to a chelant (noun) or the act of forming this bound combination (verb)
- µCi means microcuries
- mCi means millicuries
- DOTMP means 1,4,7,10-tetraazacyclododecane-1,4,7,10-tetramethylenephosphonic acid
- EDTMP means ethylenediaminetetramethylenephosphonic acid
- eq. means equivalent
- hr means hour(s)
- Kit means a vial or vials containing necessary components that are combined, following prescribed instructions, with a radioisotope to prepare a radiopharmaceutical
- FDA means US Food and Drug Administration including its regulations Mammal means warm-blooded animals including humans min. means minutes
- Phosphate buffer means pharmaceutically-acceptable mono-, di- or tri-phosphate buffer or mixtures thereof
- QC means quality control
- Radioisotopes means Sm-153, Gd-159, Ho-166, Lu-177 and Y-90 and includes their cold isotopes, a subset of radionuclides
- RCP means radiochemical purity, the proportion (expressed as percent) of the total activity of a specific radionuclide in a specific chemical or biologic form Discussion As Radioisotope-DOTMP chelates are more thermodynamically stable than are Radioisotope-EDTMP chelates; the ratio of DOTMP to Radioisotope can be as low as about 1:1 (as a safeguard 3:1 as a minimum), rather than a minimum of about 300:1 as is required for EDTMP to Radioisotope. This present formulation is used to treat a mammal having bone pain, one or more calcific tumors, or needing bone marrow suppression or bone marrow ablation.

The kit of the present invention can be used for the convenient and reliable radiopharmacy preparation of a bone-seeking radioactive lanthanide (e.g. Sm-153, Gd-159, Ho-166, Lu-177 or Y-90) chelates of DOTMP. Radiopharmacy preparation offers a crucial advantage over central manufacturing because radiolytic degradation of the formulated drug is minimized.

Three indications for the resulting present bone-seeking radiopharmaceutical formulations are envisioned. A low-dose formulation (0.5-1.0 mCi/kg) can be used to treat metastatic bone cancer arising from another primary site (e.g. prostate, breast, lung). A repeated dosing regimen has shown efficacy in treating metastatic bone cancer and the kit method can make this much more convenient.

A high-dose bone-seeking radiopharmaceutical formulation (5-30 mCi/kg) can be used to treat primary bone cancers such as osteosarcoma. These formulations may optionally be used as companion treatment to external beam radiotherapy.

A high-dose formulation (20-40 mCi/kg) can also be used to ablate bone marrow as a pretreatment for bone marrow transplant. Many diseases (e.g. myelodysplastic syndrome, leukemia, multiple myeloma, sickle cell anemia) can be treated by a successful bone marrow transplant and high dose radiopharmaceutical ablation offers a potentially safer method (compared to high dose chemotherapy and/or total body radiation).

Two different kit formulations are envisioned. A low-dose kit for the preparation of bone-seeking radiopharmaceuticals for the treatment of metastatic bone cancer and a high-dose kit for the preparation of bone-seeking radiopharmaceuticals for the treatment of osteosarcoma and for bone marrow ablation.

Low-dose kits will support the production of up to 300 mCi per vial and high-dose kits can be used to prepare up to 3 Ci per vial. Both kits reliably provide for an initial pH range of about 9-10, which is optimal for the formation of lanthanide metal DOTMP chelates, and a final pH range of about 6.5-7.5 and osmolality between 300 and 400, which make the drug suitable for injection into a patient.

When the desired Radioisotope-DOTMP complex for the present formulation is prepared, various issues arise when compared to making the Sm-EDTMP complex. After much testing it became apparent that the steps of how it is made are important to control these issues. It is difficult to manually deliver a precise volume of Radioisotope in acid solution to the Kit at the radiopharmacy where the syringe is in a shield, operated behind another shield and in a laminar flow hood. This makes it difficult to manipulate the syringe; thus making it problematic to reliably achieve the desired narrow pH range. Because of the steep titration curve in the desired pH range to form these complexes (FIG. 1), the volume of acid added must be precisely controlled. The pH also depends on the amount of metal dissolved in the HCl or $HNO_3$ and the resulting ratio of the HCl or $HNO_3$ to the NaOH or KOH. Thus as the amount of metal varies (e.g. using different activities of Radioisotope to prepare different prescribed dosages for different patients), it in turn affects both the concentration of acid (e.g. HCl or $HNO_3$) and the volume of acid required to achieve the desired pH range. This present Kit makes the reconstitution easier for a radiopharmacy to quickly, consistently and reliably obtain the desired pH. A pH range of 9-10 is required to optimally form the Radioisotope-DOTMP complex. If the pH is outside this range, then the desired complex does not form as well or can require extended manipulation such as pH adjustment or heating that results in additional time required. This can result in a low RCP and a failed QC test. If injected into a mammal, a drug with low RCP can result in a poor biodistribution of the drug in the mammal. This result can be costly or impossible to correct. The present Kit is reliable to obtain the desired pH for anywhere from trace amounts of metal up to one-third molar equivalent based on DOTMP (e.g., for 10 mg of DOTMP (18 micromoles) 6 micromoles of metal can be used) and with much larger variations in the volume of acidic Radioisotope solution added. Without the Carbonate buffer present it is very difficult to obtain the target pH range consistently.

Another issue is when calcium is added, if desired, for the reasons as noted above. In an attempt to further streamline the drug preparation, a 2 vial Kit was prepared where vial 1 had lyophilized Ca-DOTMP with excess NaOH and vial 2 had Phosphate buffer. This worked well when only trace amounts of Radioisotope were used, but the complexation did not work well when the ratio of DOTMP to metal, e.g. Sm, was about 3:1. Thus the presence of calcium created problems with forming the Radioisotope-DOTMP complex and adversely affected the RCP of the desired complex. This problem was unexpected because, as noted above, this strategy worked with Ca-EDTMP. Additionally since Sm- DOTMP is thermodynamically more stable than Ca-DOTMP it was expected that Sm would readily displace Ca in the complex as it does in the case of Ca-EDTMP.

How to overcome these issues and have a reproducible formulation for dose to a patient or mammal is one purpose of this invention. What has been found is that in contrast to the past Kits for similar drugs, for this invention it is necessary to have a Kit containing 2 to 3 vials from which the formulation is prepared. A two-part buffer system is needed to accurately control the pH during two steps of the process, first at 9-10 for optimal formation of the complex then at 7-8 for administration to a patient. Thus the Kit consists of the following: vial 1 has lyophilized Carbonate, DOTMP and NaOH or KOH. This vial is reconstituted with Radioisotope in HCl or HNO$_3$ as supplied by the manufacturer of the Radioisotope. This Radioisotope solution in aqueous HCl or HNO$_3$ is added to vial 1 where the NaOH or KOH neutralizes the HCl or HNO$_3$ and the Carbonate becomes a buffer and maintains the solution at pH 9-10 so that the complex of Radioisotope-DOTMP forms immediately with a high RCP (at least 97%). No calcium is present in the solution at this point to interfere with the kinetics of complex formation. Optional vial 2 contains Calcium solution and can be added next. Vial 3 has Phosphate buffer at about pH 7 that is added to the prior formed solution to bring the pH down to 7-8 for injection into a mammal.

The following scheme using Sm-153 is provided to assist in understanding this process. Preferably all of the process is done according to FDA requirements for a drug manufacturing process and sterile conditions using appropriate safety equipment for radioisotopes.

Vial 1 is a lyophilized mixture prepared from DOTMP (10 mg, 18.2 micromoles), and an empirically determined amount of NaOH (21.9 mg), and NaHCO$_3$ (10.7 mg) (which becomes a Carbonate buffer after the addition of acid);

Vial 1 is reconstituted with about 4.0 mL of Sm-153 (as SmCl$_3$ solution present with other Sm isotopes such as Sm-152) in 0.1 N HCl; total Sm mass per 10 mg of DOTMP must not exceed 1.38 mg (6 micromoles); the vial is then inverted or gently shaken to agitate the solution to have all solids dissolve;

A minimal QC sample (about 1-10 microliters) is removed for testing pH (expected to be 9-10) and RCP (expected to be ≥97%). Both of these values must be met to proceed. The pH is checked with pH strips and the RCP is determined using one of a number of known methods which could be used; in this present application RCP was determined using a SP Sephadex® column eluted with saline; Sm-153 activity is measured to calculate RCP by the formula:

$$RCP(\% \text{ Complex}) = \left[\frac{\mu Ci_{eluate}}{\mu Ci_{eluate} + \mu Ci_{column}}\right] \times 100;$$

Vial 2 has a solution of 36.5 mM CaCl$_2$ where 0.5 mL of this Vial 2 solution (18.2 micromole) is added to the solution of Vial 1 and inverted or gently agitated to mix the contents; although this vial is often desired, it is optional; this addition must be done prior to adding the second buffer;

Vial 3 contains 0.5 M Phosphate buffer (pH 7) as a second buffer where 0.5 mL of the solution from this Vial 3 is added to Vial 1 and inverted or gently agitated to mix the contents;

A minimal QC sample is removed for testing pH (expected to be 7-8) and RCP (expected to be ≥97%). To be suitable for use, both values must be met. The pH is checked with pH strips and the RCP is determined as before; and The activity of Sm-153-DOTMP solution is measured using a dose calibrator.

This provides the drug formulation used for injection to a mammal.

It has been found that each of these steps must be done in the order specified or undesired results occur. For example, if the Phosphate buffer is added before the Calcium solution, a precipitate of calcium phosphate will be formed even though the DOTMP chelant is present. Therefore if Calcium solution is used, it must be present in the formulated solution prior to the addition of the second buffer. If the Calcium solution in vial 2 is added to the DOTMP in vial 1 before the Sm or other Radioisotope solution is added, the calcium will interfere with the complexation. A pH of pH 9-10 is required to optimally complex the Sm with DOTMP which is not easily achieved without the Carbonate buffer. This pH is the range where the complex forms with best RCP and in the quickest time, but no other competing ions, such as calcium, should be present to interfere with the desired complex formation. The Carbonate buffer (e.g., sodium carbonate or other physiologically-acceptable Carbonate buffers or mixtures thereof) maintains this narrow pH range, buffering in the 9-10 region. Later a second buffer (sodium phosphate or other physiologically-acceptable Phosphate buffers or mixtures thereof) is used to bring the pH to 7-8 for injection of the formulated drug. Thus, to maintain pH control through this process, the Kit uses a two-part buffer system.

In some instances it has been found that the calcium is not required in the drug formulation at all. When used its main function is to prevent the DOTMP from complexing serum calcium in the body and causing a shortage of calcium that can potentially stop the heart. However, unlike prior radionuclide complex drugs, there is not the excessive amount of chelant present to be freely available to complex calcium in the body as the chelant is present in a much lower amount. Thus this concern is minimized with this DOTMP chelant.

When the drug formulation is done in this manner, there is reliably obtained a high RCP (at least 97%) and the pH and osmolarity are suitable for injection. Additionally, formulation of the drug is a rapid process to minimize radiolytic degradation.

While not wishing to be bound by theory, it is believed that the kinetics of the complex formation, the thermodynamic stability of the complex, and the lack of competing metals are critical to achieve the high RCP when the desired metals are used in the narrow pH range. Suitable metals are Sm-153, Gd-159, Ho-166, Lu-177 and Y-90, with Sm-153 or Lu-177 preferred, and Sm-153 especially preferred. It is understood that other isotopes of each metal are present with the radioactive isotope. The chelant is DOTMP.

The formulation of the present invention is in a Kit form for a radiopharmacy to use to prepare the drug according to instructions provided either with the Kit component vials or separately such as available on-line with the Kit wherein the Kit comprises: DOTMP, first buffer Carbonate and acid-neutralizing NaOH or KOH (vial 1); the Calcium solution (vial 2, optional); and the second buffer Phosphate (vial 3). The Radioisotope in HCl or HNO$_3$ would be delivered separately and then this process followed to make the drug. The components are mixed in the correct order at the appropriate time prior to use (at the hospital pharmacy or radiopharmacy). The dose may be supplied as a unit dose in a syringe for a mammal. The formulation provides a pharmaceutically-acceptable aqueous carrier for injection. The final drug may be a pharmaceutically-acceptable salt of the drug, such as sodium salt, so long as the final osmolarity is from 154 to 600, preferably 300-400 mOsm/L for injection. The drug formulation is administered to the mammal by injection intravenously.

The Components of Low-Dose and High-Dose Kits with Ranges:

Low-Dose Kits:

Vial 1 is a lyophilized mixture prepared from DOTMP (9-11 mg, preferably 10 mg), and an empirically determined amount of NaOH (19.7-24.1 mg, preferably 21.9 mg), and $NaHCO_3$ (9.7-11.8 mg, preferably 10.7 mg) (which becomes a Carbonate buffer after the addition of acid solution);

Vial 1 is reconstituted with about 3.6-4.4 mL, preferably 4.0 mL of up to 300 mCi of Sm-153 (as $SmCl_3$ solution present with other Sm isotopes such as Sm-152) in 0.1 N HCl;

Vial 2 contains a solution of 32.8-40.1 mM, preferably 36.5 mM, of $CaCl_2$ where 0.45-0.55 mL, preferably 0.5 mL, of this Vial 2 solution is added to the solution of Vial 1; although this vial is often desired, it is optional; this addition must be done prior to adding the second buffer;

Vial 3 contains 0.45-0.55 M, preferably 0.5 M, of Phosphate buffer (pH 7) as a second buffer where 0.45-0.55 mL, preferably 0.5 mL, of the solution from this Vial 3 is added to Vial 1.

High-Dose Kits:

Vial 1 is a lyophilized mixture prepared from DOTMP (90-110 mg, preferably 100 mg), and an empirically determined amount of NaOH (197-241 mg, preferably 219 mg), and $NaHCO_3$ (97-118 mg, preferably 107 mg) (which becomes a Carbonate buffer after the addition of acid solution);

Vial 1 is reconstituted with about 36-44 mL, preferably 40 mL, of up to 3000 mCi of Sm-153 (as $SmCl_3$ solution present with other Sm isotopes such as Sm-152) in 0.1 N HCl;

Vial 2 contains a solution of 328-401 mM, preferably 365 mM, of $CaCl_2$ where 4.5-5.5 mL, preferably 5 mL of this Vial 2 solution is added to the solution of Vial 1; although this vial is often desired, it is optional; this addition must be done prior to adding the second buffer;

Vial 3 contains 4.5-5.5 M, preferably 5 M, of Phosphate buffer (pH 7) as a second buffer where 4.5-5.5 mL, preferably 5 mL of the solution from this Vial 3 is added to Vial 1.

In the following examples it can be noted that staying within the desired pH range of 9 to 10 is optimal for chelation. When the pH falls to 8 or rises to 11, the RCP of the Sm-DOTMP complex is adversely affected. In the absence of the Carbonate buffer, pH can also vary even when a consistent volume of acid is added.

The invention will be further clarified by a consideration of the following examples, which are intended to be purely exemplary of the invention.

Materials and Equipment:

The radioactive isotopes were purchased from The University of Missouri Research Reactor as solutions in 0.1N HCl.

Chelants were purchased from commercial sources or were prepared as described in U.S. Pat. No. 5,059,412.

OLINDA/EXM software for internal dose assessment was acquired from the authors (Stabin M G, Sparks R B, Crowe E. (J Nucl Med. 2005 June; 46(6):1023-7).

The pH measurements were made using either an Oaktron pH700 pH meter with Mettler Toledo InLab Micro probe or with Merck MColorpHast™ pH-indicating strips (0-14).

Radioactivity was measured using a Capintec CRC-55t dose calibrator ion chamber/NaI well scintillation detector.

RCP was determined as discussed above.

General Procedure

In the following examples, the lettered examples are comparative examples or procedures, and the numbered examples are this present invention.

Example A: Preparation of Lyophilized Vials of Ca-DOTMP

Into 10 mL vials was dispensed 2.5 mL of the following solution: 1.00 g of DOTMP, 0.135 g of $Ca(OH)_2$, and 7.959 g of 10 N NaOH in 0.25 L of deionized water.

The vials were placed in a lyophilizer and freeze-dried. The amount of NaOH in these vials was empirically determined using titration experiments. It was designed to neutralize a volume of 5.0 mL of Radioisotope solution in 0.1N HCl and result in a pH of 9-10. These lyophilized vials were then used in the following examples as indicated.

Example B: Preparation of Sm-153-DOTMP from Lyophilized Ca-DOTMP, pH 11

Sm in HCl was prepared by adding 1.9 mg of non-radioactive $Sm(NO_3)_3 \cdot 6 H_2O$ along with a trace amount of Sm-153 to 6 mL of 0.1 N HCl. This was done in order to use trace amounts of activity but mimic the amount of Sm metal that would be contained in much higher clinically relevant doses. To a lyophilized Ca-DOTMP vial (prepared as in Example A) was added 4 mL (rather the 5 mL) of this Sm solution. This was done to evaluate the effect of high pH in combination with Ca on the complex formation. The resulting pH was 11 and the desired Sm-DOTMP complex was only partially formed as indicated by its RCP of 72%.

RCP was measured by adding a small drop of the sample to a 1-mL Sephadex SP® column. Complexed samarium was eluted in two 1-2 mL fractions, while free (uncomplexed) Sm was retained on the column. Radioactivity was measured in a dose calibrator, and RCP is represented as a simple ratio of activity in the combined elutions to the total activity in elutions and the column.

Example C: Preparation of Sm-153-DOTMP from Lyophilized Ca-DOTMP, pH 8

Sm in HCl was prepared by adding 1.4 mg of $Sm(NO_3)_3 \cdot 6 H_2O$ along with a trace amount of Sm-153 to 5.5 mL of 0.1 N HCl. To the lyophilized DOTMP vials (prepared as in Example A) was added 5.0 mL of this Sm solution. The pH of this Sm-DOTMP solution was 8, and RCP was 87%. This shows that the combination of Ca and pH 8 impedes complex formation. This also demonstrates that pH control by delivery of a precise volume of acid is difficult as this formulation was designed to be in the pH range 9-10.

Example D: Preparation of Ca-DOTMP Solution

A Ca-DOTMP solution was prepared from 40.4 mg of DOTMP, 5.2 mg of $Ca(OH)_2$, and 318.6 mg of 10 N NaOH, which volume was brought to a total volume of 10 mL with deionized water. The amount of NaOH in 2.5 mL of this solution was calculated based on prior titration experiments, to neutralize 5.0 mL of Radioisotope solution in 0.1N HCl and result in a pH of 9-10.

Example E: Preparation of DOTMP Solution

A DOTMP solution was prepared without calcium using 40.2 mg of DOTMP and 202.0 mg of 50% NaOH in 10 mL of deionized water. The amount of NaOH in 2.5 mL of this solution was calculated based on prior titration experiments, to neutralize 5.0 mL of Radioisotope solution in 0.1N HCl and result in a pH of 9-10.

Example F: Preparation of Sm-153-DOTMP from Ca-DOTMP Solution

The Ca-DOTMP solution (prepared as in Example D) was tested by adding Sm solution to 2.5 mL of that solution. The Sm solution was prepared from 2.6 mg of $Sm(NO_3)_3 \cdot 6 H_2O$, along with a trace amount of Sm-153 in 4 mL of 0.1 N HCl. All 4 mL was then added to the 2.5 mL of the DOTMP solution. Its pH was 11, so additional 0.1 N HCl was slowly added until the pH reached 9. About 0.2 mL was required to adjust the pH.

Despite adjusting to the desired pH, RCP was only 88%. This shows that, even in the desired pH range, the presence of Ca interferes with the complex formation. This also again demonstrates that achieving this target pH range can be difficult as the total volume of acid added, 4.2 mL, is less that the anticipated 5.0 mL.

Example G: Titration of DOTMP

DOTMP (10 mg) was dissolved in 10 N NaOH (72.6 mg) and deionized water (1 mL) in a 20 mL vial. This solution was titrated with 0.1N HCl. These results are shown in Table 1 and in FIG. 1. These results demonstrate the difficulty of achieving the desired pH range upon reconstitution in the absence of Carbonate buffer.

TABLE 1

Titration of DOTMP containing NaOH

| 0.1N HCl (mL) | pH |
| --- | --- |
| 2.0 | 13.39 |
| 2.2 | 13.32 |
| 2.4 | 13.24 |
| 2.6 | 13.15 |
| 2.8 | 13.04 |
| 3.0 | 12.94 |
| 3.2 | 12.80 |
| 3.4 | 12.64 |
| 3.6 | 12.41 |
| 3.8 | 12.05 |
| 4.0 | 10.87 |
| 4.1 | 10.40 |
| *4.2* | *9.26* |
| 4.3 | 8.53 |
| 4.4 | 7.78 |
| 4.5 | 6.93 |
| 4.6 | 6.31 |
| 4.7 | 5.82 |
| 4.8 | 5.15 |

The results show that there is no buffering in this formulation within the range of pH 9-10, which is optimal for Sm-DOTMP complex formation. The bold italicized box indicates the preferred pH range. Very precise measurement of acid is required to achieve this pH. This is difficult in the case of radioactive compounds as they must be handled in a shielded system that makes such precise measurements challenging.

Example 1: Preparation of Lyophilized DOTMP Containing Carbonate

Into 10 mL vials was dispensed 2.5 mL of a solution prepared by combining 99.9 mg of DOTMP, 726.5 mg of 10 N NaOH, and 107.3 mg of $NaHCO_3$ in 25 mL of deionized water. The vials were placed in a lyophilizer and freeze-dried. The amount of NaOH in these vials was empirically determined using titration experiments. It was designed to neutralize a volume of 4.0 mL of Radioisotope solution in 0.1N HCl and buffer in the pH range of 9-10.

Example 2: Titration of Lyophilized DOTMP Containing Carbonate

Figure 2:
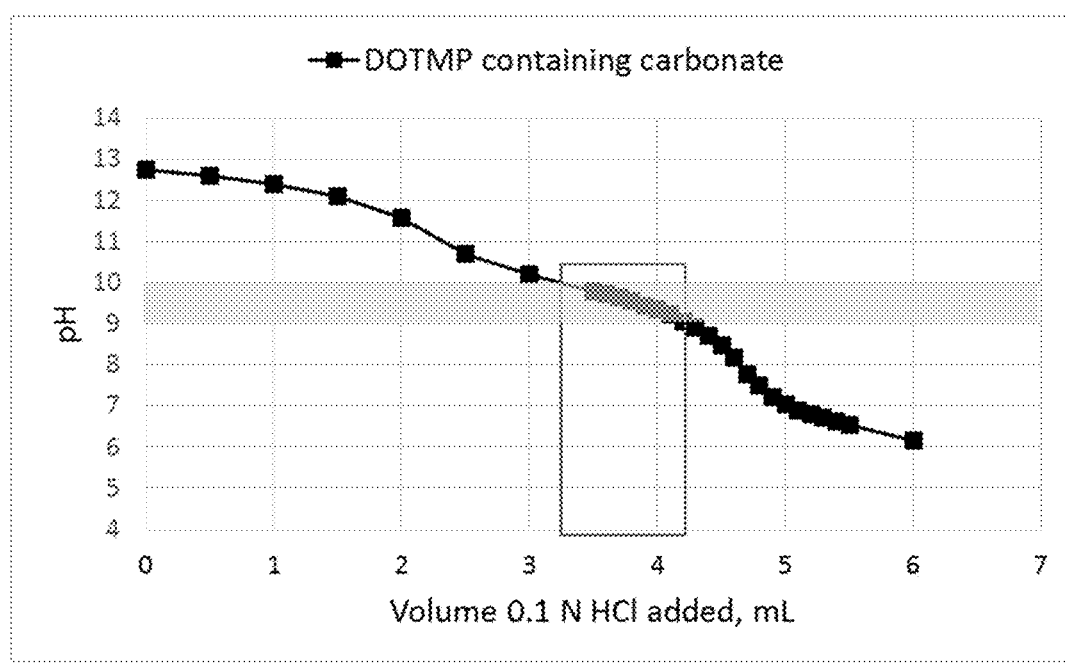
FIG. 2 graphically shows the data for Carbonate, NaOH and DOTMP titrated with 0.1 N HCl. The desired pH range of 9-10 can be achieved using a relatively wide variation in acid volume thereby making radiopharmacy preparation of the drug reliably reproducible.

A lyophilized vial of DOTMP containing Carbonate (prepared as in Example 1) was titrated with 0.1 N HCl. The Carbonate was shown to have buffering capability in the region of interest, pH 9-10 (see Table 2 and FIG. 2). FIG. 2 shows this titration curve highlighting in grey the desired pH range for the optimal formation of the complex. Contrast this with the titration curve of DOTMP without Carbonate buffer in FIG. 1 (from Example G). The slope of the curve in FIG. 1 makes it difficult to always achieve the desired pH without very precise delivery of acid; whereas the shallow slope in FIG. 2 enables the desired pH range to be more readily obtained.

TABLE 2

Titration of lyophilized DOTMP containing Carbonate and NaOH

| 0.1N HCl (mL) | pH |
| --- | --- |
| 1 | 13.05 |
| 2 | 12.52 |
| 2.5 | 12.12 |
| 2.7 | 11.83 |
| 2.9 | 11.37 |
| 3.1 | 10.82 |
| 3.2 | 10.59 |
| 3.3 | 10.44 |
| 3.4 | 10.28 |
| 3.5 | 10.15 |
| 3.6 | 10.04 |
| *3.7* | *9.92* |
| *3.8* | *9.8* |
| *3.9* | *9.69* |
| *4* | *9.56* |
| *4.1* | *9.41* |
| *4.2* | *9.25* |
| 4.4 | 8.8 |
| 4.6 | 8.07 |
| 4.8 | 7.33 |
| 5 | 6.89 |

The results show that the Carbonate present in the formulation of Example 1 buffers within the range of pH 9-10, which is optimal for Sm-DOTMP complex formation. The bold italicized boxes indicate the preferred pH range.

Example 3: Preparation of Sm-153 DOTMP with Added Ca

A vial prepared as in Example 1 was reconstituted by adding 4.0 mL of a trace Sm-153 solution in 0.1N HCl prepared as in Example B. The pH was 10 and the RCP was 99.7%. To this vial was added 0.5 mL 36.5 mM $CaCl_2$. To the resulting solution in this vial was next added 0.5 mL 0.5 M Phosphate. The pH was 7 and the RCP was 99.8%.

Example 4: Preparation of Sm-153-DOTMP without Added Ca

A vial prepared as in Example 1 was reconstituted by adding 4.0 mL of a trace Sm-153 solution in 0.1N HCl prepared as in Example B. The pH was 10 and the RCP was 99.9%. To this vial was added 0.5 mL 0.5 M Phosphate. The pH was 7 and the RCP was 99.9%.

Example 5: Rat Biodistribution

The formulations prepared in Example 3 (w/Ca) and Example 4 (w/out Ca) were each injected into the tail veins of three male Sprague-Dawley rats. The rats weighed between 230 and 245 g each. After 2 hr, the rats were sacrificed and the following organs and tissues were collected: blood, heart, lung, femur, muscle, liver, spleen, kidney, small intestine, large intestine, stomach and brain. Also collected were urine, feces, and the remainder of the body. The radioactivity in each of these samples was measured and the percent injected dose (% ID) in each was calculated. The results are shown in Table 3.

TABLE 3

Biodistribution of Sm-153-DOTMP both with and without added Ca

| | Formulation of Example 3 | Formulation of Example 4 |
|---|---|---|
| Blood | 0.0% | 0.1% |
| Heart | 0.0% | 0.0% |
| Lung | 0.0% | 0.0% |
| Bone | 50.0% | 51.6% |
| Muscle | 0.1% | 0.1% |
| Liver | 0.1% | 0.1% |
| Spleen | 0.0% | 0.0% |
| Kidney | 0.5% | 0.6% |
| Sm Int | 0.7% | 2.5% |
| Lg. Int | 0.6% | 0.1% |
| Stomach | 0.0% | 0.6% |
| Brain | 0.0% | 0.0% |
| Bladder/Urine | 46.2% | 39.9% |

These results demonstrate that the formulations of the present invention both with and without added Ca have a favorable biodistribution for a therapeutic bone agent (e.g., high bone uptake, low soft tissue uptake, and rapid clearance of the activity not associated with bone).

Example 6: Process of Kit Formation

The following process scheme is provided to assist in understanding the steps in this process. All of the process is done according to FDA requirements for a drug manufacturing process and using sterile conditions, and safety handling for radioactive drugs and isotopes.

Vial 1 contains a lyophilized mixture prepared from DOTMP (10 mg), NaOH (21.9 mg), and NaHCO$_3$ (10.7 mg, to form the Carbonate buffer);

Vial 1 is reconstituted with 4 mL of Sm-153 (as SmCl$_3$ solution) in 0.1 N HCl; total Sm mass per 10 mg of DOTMP must not exceed 1.38 mg;

Vial 1 is then inverted (or gently shaken) to agitate the solution and have all solids dissolve;

A minimal QC sample (1-10 microliter) is removed for testing the pH (expected to be 9-10) and RCP (expected to be ≥97%). The pH is checked with a pH strip and the RCP is determined using a SP Sephadex® column eluted with saline; Sm-153 activity is measured to calculate RCP by the formula:

$$RCP(\%\ \text{Complex}) = \left[\frac{\mu Ci_{eluate}}{\mu Ci_{eluate} + \mu Ci_{column}}\right] \times 100;$$

Vial 2 has a solution of 36.5 mM CaCl$_2$ where 0.5 mL of this Vial 2 solution is added to the solution of Vial 1 and inverted to mix the contents; although this vial is often desired, it is optional; this addition must be done prior to adding the second buffer;

Vial 3 contains 0.5 M sodium phosphate (pH 7) as a second buffer where 0.5 mL of the solution from Vial 3 is added to Vial 1 and inverted to mix the contents;

A minimal QC sample is removed for testing the pH (expected to be 7-8) and RCP (expected to be ≥97%) as before; and The activity of Sm-153-DOTMP complex solution is measured using a dose calibrator.

Example 7

A vial prepared as in Example 1 was reconstituted by adding 4.0 mL of a solution containing 307 mCi of Sm-153 in 0.1N HCl. The pH was between 9 and 10 and the RCP was 98.6%. To this vial was added 0.5 mL 36.5 mM of CaCl$_2$. To the resulting solution in this vial was next added 0.5 mL of 0.5 M Phosphate. The solution was filtered through a 0.2 μm filter into a sterile 10 mL vial. The final formulation contained 269.5 mCi, the pH was 7 and the RCP was 98.0%.

Example 8: Treatment of Osteosarcoma and Myelodysplastic Syndrome

A 25-year-old, 60 kg male patient presenting with both recurrent inoperable osteosarcoma and myelodysplastic syndrome was in need of a bone marrow transplant. He was injected with a diagnostic dose, 1 mCi/kg (60 mCi) of the formulation of Example 7. The purpose of this diagnostic dose was to calculate the radiation dose to the marrow and other organs for a proposed ablative dose prior to bone marrow transplantation.

A SPECT scan (Single Photon Emission Computed Tomography) at 1 hr revealed that the Sm-153 was roughly evenly distributed between the skeletal system and the bladder and kidneys. No other soft tissue showed any activity. The kidneys and bladder were not visible in the 24-hr, 48-hr and 7-day images. Long-term skeletal activity follows the radioactive half-life of Sm-153 (i.e., Sm-153-DOTMP remains bound to bone).

Using the skeletal uptake and clearance data, OLINDA 1.1 dosimetry software was used to estimate that for a myeloablative dose of 30 mCi/kg (1800 mCi), the estimated radiation dose would be 38 Gy to red marrow and 8 Gy to kidneys. No other organs were expected to receive a significant radiation dose. These estimates showed that the marrow could be safely ablated using the planed dose.

Example 9: Preparation of High Dose Formulation from Kit

Nine vials prepared as in Example 1 were reconstituted by adding to each 4.0 mL of a solution containing 237 mCi of Sm-153 in 0.1N HCl (total activity 2.1 Ci). The pH of each solution was between 9 and 10 and the RCP of each was between 98 and 100%. To each vial was added 0.5 mL of 36.5 mM $CaCl_2$ followed by 0.5 mL of 0.5 M Phosphate. The solutions were filtered through a 0.2 μm filter into a sterile 100 mL vial. The final formulation contained 1,972 mCi, the pH was 7 and the RCP was 98.8%.

Example 10: Treatment of the Patient with High Dose Kit

The patient of Example 8 was infused with 1.9 Ci of the formulation of Example 9 in order to ablate the bone marrow to allow for subsequent bone marrow transplantation. The estimated radiation dose is 40 Gy to red marrow and 9 Gy to kidneys. The 48 hr image revealed no soft tissue activity and only bone uptake was visible.

Bone marrow biopsy fourteen days post ablative dose revealed that bone marrow had been successfully ablated. Stem cells from a matched donor were administered. Clinical indicators such as white blood cell count, red blood cell count and platelet count indicated successful resolution of myelodysplastic syndrome.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

What is claimed is:

1. A process for the preparation of a pharmaceutically-acceptable drug formulation using a kit, wherein a kit means a vial or vials containing necessary components that are combined, following prescribed instructions, with a radioisotope to prepare a radiopharmaceutical, comprising at least three components, having a two-part buffering system, including instructions for its use, for preparing a pharmaceutically-acceptable drug formulation of a radioisotope-DOTMP chelate, wherein the radioisotope is Sm-153, Gd-159, Ho-166, Lu-177, and Y-90 and includes their cold isotopes, a subset of radionuclides, DOTMP is 1,4,7,10-tetracyclododecane-1,4,7,10-tetramethylenephosphonic acid, and wherein the kit components are:

vial 1: lyophilized mixture of from 9-11 mg of DOTMP, from 9.7-11.8 mg of carbonate, which is pharmaceutically-acceptable $NaHCO_3$, $Na_2CO_3$, $KHCO_3$ or $KCO_3$ and mixtures thereof which, under appropriate conditions, have the ability to buffer at pH 9-10, and an empirically determined amount of from about 19.7-24.1 mg of NaOH or KOH; which becomes a carbonate buffer after the addition of acid;

vial 2: a calcium solution, which is an aqueous solution of calcium that can be prepared from calcium chloride or calcium nitrate in a pharmaceutically-acceptable aqueous solvent; and vial 3: a phosphate buffer, which is a pharmaceutically-acceptable mono-, di- or tri-phosphate buffer or mixtures thereof, in a pharmaceutically-acceptable aqueous solvent at a pH of about 7, optionally with pharmaceutically-acceptable preservatives, diluents, and excipient;

provided that when the kit is constituted to form the drug at the time of use, a radioisotope is added to vial 1 to achieve a pH of 9-10 and then adding vial 2 and vial 3 to form the drug, which process to make the drug comprises the steps of:

a) reconstituting the lyophilized vial 1 having carbonate, DOTMP and NaOH or KOH, with about 3.6-4.4 mL of a radioisotope in HCl or $HNO_3$; and wherein the carbonate buffers at pH to about 9-10 so that the radioisotope-DOTMP complex forms readily with an initial RCP, meaning radiochemical purity, the proportion expressed as percent of the total activity of a specific radionuclide in a specific chemical or biologic form, of at least 97%;

b) adding to vial 1, vial 2, a solution of 32.8-40.1 mM of calcium solution, to the radioisotope-DOTMP of step a); and c) adding vial 3, containing about 0.45-0.55 M phosphate buffer, to the prior formed solution of step b) to bring the pH to about 7-8 suitable for injection into a mammal.

2. The process of claim 1, wherein the drug formulation is a low dose formulation:

vial 1 is a lyophilized mixture prepared from about 10 mg of DOTMP, and an empirically determined amount of about 21.9 mg of NaOH, and from about 10.8 mg of $NaHCO_3$;

vial 1 is reconstituted with about 4.0 mL of up to 300 mCi of radioisotope in 0.1 N HCl;

vial 2 contains a solution of 36.5 mM of $CaCl_2$) where 0.5 mL of this vial 2 solution is added to the solution of vial 1; this addition must be done prior to adding the second buffer; and vial 3 contains 0.5 M phosphate buffer pH 7 as a second buffer, wherein 0.45-0.55 mL of the solution from this vail 3 is added to vial 1.

3. The process of claim 1, wherein the drug formulation is a high dose formulation:

vial 1 is a lyophilized mixture of from 90-110 mg DOTMP, and an empirically determined amount of from about 197-241 mg NaOH, and an empirically determined amount of from about 97-118 mg $NaHCO_3$, which becomes a carbonate buffer after the addition of acid;

vial 1 is reconstituted with about 36-44 mL, preferably 40 mL of up to 3000 mCi Sm-153, as $SmCl_3$ solution present with other Sm isotopes such as Sm-152 in 0.1N HCl;

vial 2 contains a solution of 328-401 mM, of $CaCl_2$) where 4.5-5.5 mL, of this vial 2 solution is added to the solution of vial 1; this addition must be done prior to adding the second buffer; and vial 3 contains 4.5-5.5 M, phosphate buffer at about pH 7 as a second buffer where 4.5-5.5 mL, of the solution from this vial 3 is added to vial 1.

4. The process of claim 1 wherein step a) the radioisotope is Sm-153 or Lu-177.

* * * * *